United States Patent [19]
Pak

[11] Patent Number: 5,952,367
[45] Date of Patent: Sep. 14, 1999

[54] METHOD OF TREATING PAIN CAUSE BY BURSITIS TENDINITIS ARTHRITIS

[76] Inventor: Kyoungsik Pak, 371 Sweetbriar Rd., King of Prussia, Pa. 19406

[21] Appl. No.: 08/842,967

[22] Filed: Apr. 25, 1997

[51] Int. Cl.$^6$ .................. A61K 31/40; A61K 31/195; A61K 31/19; A61K 31/16
[52] U.S. Cl. .................. 514/420; 514/562; 514/569; 514/570; 514/629
[58] Field of Search .................. 514/562, 570, 514/420, 569, 629

[56] References Cited

U.S. PATENT DOCUMENTS 5,053,429  10/1991  Hirsch et al. .................. 514/562

*Primary Examiner*—William R. A. Jarvis
*Attorney, Agent, or Firm*—John F. A. Earley; John F. A. Earley, III; Harding, Earley, Follmer & Frailey

[57] ABSTRACT

Disclosed herein is a method of treating pain caused by bursitis, tendinitis, arthritis, and the like, comprises ingesting an effective amount of a non-steroidal anti-inflammatory drug, and ingesting an effective amount of L-or DL-Methionine and a sugar which provides relief from stomach discomfort caused by the non-steroidal anti-inflammatory drug and which in combination with the non-steroidal anti-inflammatory drug results in relieving the pain more effectively than the non-steroidal anti-inflammatory drug alone.

6 Claims, No Drawings

METHOD OF TREATING PAIN CAUSE BY BURSITIS TENDINITIS ARTHRITIS

BACKGROUND OF THE INVENTION

1. Field of the Invention

This invention relates to the field of treating pain caused by bursitis, tendinitis, arthritis, and the like, and is specifically concerned with a composition for treating such pain, a dosage unit for treating such pain, and a method of treating such pain.

2. Description of the Prior Art

To ease the pain suffered by bursitis, tendinitis, arthritis, and the like, millions of people ingest daily high doses of non-steroidal anti-inflammatory drugs (hereinafter called "NSAIDs") such as ibuprofen. Unfortunately, NSAIDs irritate the stomach and the intestines in many people causing ulcers and bleeding. It has been reported in the *Archives of Internal Medicine* that ulcers and gastrointestinal bleeding caused by NSAIDs lead to as many as 20,000 deaths each year.

SUMMARY OF THE INVENTION

It is an object of the invention to provide a composition, a dosage unit thereof, and a method for treating pain caused by bursitis, tendinitis, arthritis, and the like.

Further, it is an object of the invention to provide a composition, a dosage unit thereof, and a method of treating pain caused by bursitis, tendinitis, arthritis, and the like, which helps relieve stomach discomfort caused by ingestion of NSAIDs.

Further, it is an object of the invention to provide a composition, a dosage unit thereof, and a method of treating pain caused by bursitis, tendinitis, arthritis, and the like, which enhances the effectiveness of the NSAIDs in relieving the pain.

These an other objects of the invention are accomplished by my invention which is described below.

DETAILED DESCRIPTION

In accordance with the invention, a composition for treating pain caused by bursitis, tendinitis, arthritis, and the like, comprises a non-steroidal anti-inflammatory drug (hereinafter called "NSAID"), L- or DL-Methionine, and an optional sweetener.

The invention also includes a dosage unit for treating pain caused by bursitis, tendinitis, arthritis, and the like, which comprises an effective dosage of a non-steroidal anti-inflammatory drug (NSAID) and L- or DL-Methionine. Optionally, the dosage unit may include an effective amount of a sweetener.

Further, the invention includes a method of treating pain caused by bursitis, tendinitis, arthritis, and the like, which comprises the steps of ingesting an effective amount of a non-steroidal anti-inflammatory drug (NSAID), and ingesting an effective amount of L- or DL-Methionine. Optionally, the method includes the additional step of ingesting an effective amount of a sweetener.

Exemplary of the non-steroidal anti-inflammatory drug (NSAID), which functions as a pain reliever, are indomethacin, naproxen, ketoprofen, paracetamol, ibuprofen, flurbiprofen, and the like.

The L- or DL-Methionine provides relief from any stomach discomfort caused by ingestion of the NSAID. DL-Methionine is preferred.

The combination of an effective amount of a non-steroidal anti-inflammatory drug (NSAID) with an effective amount of Methionine, whether L-Methionine or DL-Methionine, ingested in accordance with the invention, results in the significant enhancement of the effectiveness of the NSAID in relieving the pain caused by bursitis, tendinitis, arthritis, and the like. That is, the pain caused by bursitis, tendinitis, arthritis, and the like is reduced more by ingesting the combination of a non-steroidal anti-inflammatory drug (NSAID) and Methionine than by ingesting a non-steroidal anti-inflammatory drug (NSAID) alone. This is completely unexpected.

The sweetener may be fructose, dextrose, sucrose, saccharin, or the like, for example, and preferably is fructose which is sweeter than sucrose and which may be eaten by diabetics.

As used in this application, the term "dosage unit" comprises the amount of NSAID, L- or DL-Methionine, and sweetener (if any) to be ingested by the patient in a single treatment period. A treatment period may comprise (a) simultaneous ingestion of the NSAID, L- or DL-Methionine, and sweetener (if any), or (b) the sequential ingestion of these components over a few seconds to up to a period of about 1 or 2 hours. Treatment may comprise a single treatment period, or multiple treatment periods for a day (e.g., 3 times per day), or several days, or longer.

The form of the dosage unit may comprise (a) one or more tablets or capsules each comprising an effective amount of an NSAID, L- or DL-Methionine, and sweetener (if any), (b) one or more individual tablets or capsules for each of the components of the inventive dosage unit, and (c) other forms known in the art for ingestion of medicines and the like. For example, one such known form comprises the NSAID in tablet form and the L- or DL-Methionine in liquid form made by mixing the effective amount of L- or DL-Methionine into water (e.g., about 2 ounces of water), and I refer to my U.S. patent application Ser. No. 08/591,889, filed on Jan. 25, 1996, now U.S. Pat. No. 5,703,127, which is incorporated herein by reference.

Preferably, the amount of the NSAID in a dosage unit is the amount of the NSAID prescribed by a doctor or recommended by the NSAID manufacturer for ingestion by a patient taking the NSAID to relieve pain caused by bursitis, tendinitis, arthritis, and the like.

Preferably, the dosage of L- or DL-Methionine is about 500 mg to about 1500 mg, and more preferably is 1000 mg.

If the dosage unit includes a sweetener, preferably, the dosage of sweetener is about 1000 mg to about 3000 mg, and more preferably is in a range of about 1000 mg to about 2000 mg. However, the amount of sweetener may be outside these ranges.

I now turn to the examples of the invention, all ingredients being by weight unless indicated otherwise.

EXAMPLE 1

Patients suffering from pain caused by bursitis, tendinitis, arthritis, and the like are treated for this pain by ingesting 400 mg of ibuprofen and 1 gram of DL-Methionine three times a day for a week.

Prior to beginning this treatment, the patients took 400 mg to 800 mg of ibuprofen 3 times a day for several days to about one week without obtaining adequate relief from the pain caused by bursitis, tendinitis, arthritis, and the like, and suffered from the stomach discomfort caused by the ingestion of the NSAID.

The patients reported that treatment with the NSAID and the DL-Methionine relieved the pain caused by bursitis, tendinitis, arthritis, and the like, and that stomach and intestinal pains associated with taking the NSAID did not develop. The patients further reported obtaining a comfortable and relaxed overall feeling or sensation, as well as sleeping well following treatment with the NSAID in combination with the DL-Methionine.

EXAMPLE 2

A patient suffering from pain caused by bursitis in his elbow ingested 100 mg of flurbiprofen twice a day after meals for three days. However, the patient reported that the pain was not relieved and continued, and that unbearable stomach pains had developed. Following ingestion of the last dosage of flurbiprofen, the patient ingested 1 gram of DL-Methionine. The patient reported that five hours later the pain in his elbow and the pain in his stomach both were relieved.

The following Examples 3–8 further illustrate the invention. In these examples, patients suffering from pain caused by bursitis, tendinitis, arthritis, and the like are treated for this pain by ingesting the dosage unit of the example as needed, resulting in relief of the pain without the development of stomach and intestinal discomfort associated with ingesting an NSAID.

EXAMPLE 3

| COMPONENT | QUANTITY |
| --- | --- |
| ibuprofen | 400 mg |
| DL- Methionine | 500 mg |

EXAMPLE 4

| COMPONENT | QUANTITY |
| --- | --- |
| ibuprofen | 400 mg |
| DL- Methionine | 1500 grams |

EXAMPLE 5

| COMPONENT | QUANTITY |
| --- | --- |
| ibuprofen | 400 mg |
| L- Methionine | 500 mg |

EXAMPLE 6

| COMPONENT | QUANTITY |
| --- | --- |
| ibuprofen | 400 mg |
| L- Methionine | 1000 mg |

EXAMPLE 7

| COMPONENT | QUANTITY |
| --- | --- |
| ibuprofen | 400 mg |
| L- Methionine | 1500 grams |

EXAMPLE 8

| COMPONENT | QUANTITY |
| --- | --- |
| ibuprofen | 400 mg |
| DL- Methionine | 1000 grams |
| Fructose | 1500 mg |

The sweetener eliminates the unpleasant taste of the Methionine. With the inclusion of a sweetener, side effects such as indigestion, weakness, and unpleasant feeling which sometimes occur with ingesting Methionine, occur less frequently and with less severity. Reference again is made to my U.S. patent application Ser. No. 08/591,889, now U.S. Pat. No. 5,703,127, which is incorporated herein by reference.

In this Example 8, the ibuprofen is ingested in tablet form, and the Methionine and sweetener are mixed into 2 ounces of water, and the Methionine/sweetener solution is ingested.

I claim:

1. A method of treating pain caused by bursitis, tendinitis, or arthritis, and of relieving stomach irritation associated with ingestion of non-steroidal anti-inflammatory drugs, comprising ingesting an effective amount of a non-steroidal anti-inflammatory drug, ingesting L- or DL-Methionine in an amount in a range of about 500 mg to about 1500 mg, ingesting a sweetener in an amount in a range of about 1000 mg to about 3000 mg, relieving with the L- or DL-Methionine stomach irritation caused by ingestion of the non-steroidal anti-inflammatory drug, reducing with the sweetener the frequency and severity of undesirable side effects of the L- or DL-Methionine, and relieving the pain caused by bursitis, tendinitis, or arthritis more effectively with the non-steroidal anti-inflammatory drug and the L- or DL-Methionine than with the non-steroidal anti-inflammatory drug alone.

2. The method of claim 1, the sweetener being fructose, dextrose, sucrose, or saccharin.

3. The method of claim 1, the non-steroidal anti-inflammatory drug being indomethacin, naproxen, ketoprofen, paracetamol, ibuprofen, or flurbiprofen.

4. The method of claim 1, the amount of L- or DL-Methionine being about 1000 mg.

5. The method of claim 3, the sweetener being fructose, dextrose, and sucrose, or saccharin.

6. The method of claim 5, the amount of the L- or DL-Methionine being 1000 mg, and the amount of the sweetener being about 1500 mg.

* * * * *